US009415144B2

(12) United States Patent
Anzai et al.

(10) Patent No.: US 9,415,144 B2
(45) Date of Patent: Aug. 16, 2016

(54) ANTITHROMBOTIC MATERIAL AND MEDICAL DEVICE

(71) Applicant: TERUMO KABUSHIKI KAISHA, Shibuya-ku (JP)

(72) Inventors: Takao Anzai, Shizuoka (JP); Tomoe Hakamatani, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/186,124

(22) Filed: Feb. 21, 2014

(65) Prior Publication Data

US 2014/0172117 A1    Jun. 19, 2014

Related U.S. Application Data

(63) Continuation of application No. PCT/JP2012/069739, filed on Aug. 2, 2012.

(30) Foreign Application Priority Data

Aug. 22, 2011  (JP) ................................. 2011-180925
Nov. 9, 2011   (JP) ................................. 2011-245614
Feb. 9, 2012   (JP) ................................. 2012-026401

(51) Int. Cl.
*C08L 33/26* (2006.01)
*A61L 27/34* (2006.01)
(Continued)

(52) U.S. Cl.
CPC ................ *A61L 33/068* (2013.01); *A61F 2/04* (2013.01); *A61L 27/34* (2013.01); *A61L 29/085* (2013.01); *A61L 31/10* (2013.01); *A61L 33/064* (2013.01)

(58) Field of Classification Search
None
See application file for complete search history.

(56) References Cited

U.S. PATENT DOCUMENTS 4,663,364 A  *  5/1987  Iwasaki ................... A01N 25/04
                                                            106/18.31
4,731,080 A  *  3/1988  Galin ...................... A61F 2/1613
                                                            427/2.24
(Continued)

FOREIGN PATENT DOCUMENTS

JP          9-131396 A      5/1997
JP       2001-145695 A      5/2001
(Continued)

OTHER PUBLICATIONS

International Search Report (PCT/ISA/210) mailed on Sep. 4, 2012, by the Japanese Patent Office as the International Searching Authority for International Application No. PCT/JP2012/069739.
(Continued)

*Primary Examiner* — Peter A Salamon
(74) *Attorney, Agent, or Firm* — Buchanan, Ingersoll & Rooney PC (57) ABSTRACT

An antithrombotic material has an excellent anticoagulant activity and can form a stable coating layer on a base material through a simple and mild coating process. An antithrombotic material includes a copolymer configured to have 75% by mole to 25% by mole of a repeating unit (A) derived from diacetone(meth)acrylamide represented by the following formula (1) (wherein $R^1$ is a hydrogen atom or a methyl group) and 25% by mole to 75% by mole of a repeating unit (B) derived from a monomer having at least one sulfonate group selected from a group consisting of 2-(meth)acrylamide-2-methyl-propane sulfonic acid, vinyl sulfate, allyl sulfate, styrenesulfonic acid, sulfoethyl(meth)acrylate, and sulfopropyl (meth)acrylate in a molecule, or a salt of the monomer (the total amount of the repeating unit (A) and the repeating unit (B) is 100% by mole).

18 Claims, 2 Drawing Sheets

(51) Int. Cl.
*A61L 31/10* (2006.01)
*A61F 2/04* (2013.01)
*A61L 33/06* (2006.01)
*A61L 29/08* (2006.01)

(56) References Cited

U.S. PATENT DOCUMENTS

| | | | | |
|---|---|---|---|---|
| 4,739,008 A * | 4/1988 | Robinson | ............... | C08F 2/32 524/801 |
| 4,872,867 A | 10/1989 | Joh | | |
| 5,278,200 A | 1/1994 | Coury et al. | | |
| 6,540,698 B1 * | 4/2003 | Ishii | ............... | A61L 31/10 600/435 |
| 6,555,225 B1 * | 4/2003 | Yoshioka | ............... | A61L 33/00 427/180 |
| 2005/0107527 A1 | 5/2005 | Holub et al. | | |
| 2009/0035350 A1 * | 2/2009 | Stankus | ............... | A61L 27/18 424/424 |
| 2009/0234090 A1 * | 9/2009 | Ogawa | ............... | C09D 133/26 526/304 |

FOREIGN PATENT DOCUMENTS

| | | |
|---|---|---|
| JP | 2009-216572 A | 9/2009 |
| WO | WO 00/06651 A1 | 2/2000 |

OTHER PUBLICATIONS

Extended European Search Report dated Mar. 2, 2015, issued by the European Patent Office in the corresponding European Application No. 12825135.2. (8 pages).

Office Action (Notice of Reasons for Rejection) issued by the Japanese Patent Office in corresponding Japanese Patent Application No. 2013-529949 on Jan. 26, 2016 (9 pages including English translation).

* cited by examiner

ANTITHROMBOTIC MATERIAL AND MEDICAL DEVICE

CROSS REFERENCES TO RELATED APPLICATIONS

This application claims priority as a continuation application under 35 U.S.C. §120 to International Application No. PCT/JP2012/069739 filed on Aug. 2, 2012, designating the U.S., and which claims priority to Japanese Application No. 2011-180925 filed on Aug. 22, 2011, Japanese Application No. 2011-245614 filed on Nov. 9, 2011, and Japanese Application No. 2012-026401 filed on Feb. 9, 2012, the entire content of which is incorporated herein by reference.

TECHNICAL FIELD

The present disclosure relates to an antithrombotic material and a medical device coated with the antithrombotic material.

BACKGROUND DISCUSSION

Various medical devices used in a living body such as an artificial blood vessel, artificial organs or the like can require affinity for blood, body fluids, or a living tissue. Among them, antithrombogenicity preventing blood from clotting is important in a medical device coming into contact with blood.

In general, antithrombogenicity is provided to a medical device by performing a method for coating a base material for forming a medical device with an antithrombotic material, or a method for fixing an antithrombotic material on a surface of a base material.

For example, a method has been known in which the absorption of a biogenic component to the surface of the base material is physicochemically inhibited and the formation of the thrombus on the surface of the base material is inhibited, by graft-polymerizing a water-soluble polymer material on the surface of the base material. However, there have been problems with the method that the blood plasma protein enters the surface-grafted layer over time, coagulation due to a blood plasma component or a platelet activated on the surface of the base material influences a living body, and the like. Furthermore, there are also problems that the production process of the method is complicated and there is a great restriction in view of the type of the base material to be grafted.

In addition, another method also has been known in which the antithrombogenicity is provided to the surface of the base material by fixing a material such as heparin having anticoagulant activity on the surface of the base material, or by sustainably releasing the aforementioned material from the surface of the base material. However, there are problems with the biological substance such as the heparin that the anticoagulant activity of the biological substance deteriorates by sterilization treatment after fixing the biological substance on the surface of the base material, the biological substance is decomposed by enzyme in a living body so that the activity cannot be maintained for a long period of time, and it is impossible to apply to compounds other than the heparin having the anticoagulant activity in view of safety issues.

In contrast to the above, a sulfonate group-containing polymer such as a poly-2-acrylamide-2-methyl propane sulfonic acid (PAMPS) has been known as the antithrombotic material which is excellent in the anticoagulant activity and sterilization resistance and which can improve safety and durability.

As a method for fixing the PAMPS on the surface of the base material, for example, Patent Literature 1 discloses a method for fixing the PAMPS on the surface of the base material such that a 2-acrylamide-2-methylpropanesulfonic acid (AMPS)-acrylic acid copolymer is coated after coating a polymer (reactive compound), which has an epoxy group or an isocyanate group reacting with a carboxyl group, on the surface of the base material, and the epoxy group or the isocyanate group is reacted with the carboxyl group by heating or the like to form a chemical bond.

Meanwhile, the medical device can require having a lubricating surface for the purpose of reducing tissue damage or improving operability. As an example of the surface lubrication, Patent Literature 2 discloses a method for forming a surface lubrication layer containing a reaction product between a hydrophilic polymer compound and a cross-linking agent including a hydrazide compound. In addition, according to the method, it is possible to provide the lubricity and the antithrombogenicity to the surface of the base material by performing the surface lubrication treatment in coexistence with a water-soluble physiologically active substance such as the heparin.

Patent Literature 1: JP-A-09-131396
Patent Literature 2: U.S. Pat. No. 6,540,698

However, since the method disclosed in Patent Literature 1 requires heating for the reaction between the epoxy group or the isocyanate group and the carboxyl group to fix the antithrombotic material on the surface of the base material, there is a problem that the type or the form of the base material is limited. Furthermore, since the method utilizes the reaction between a highly reactive proton-accepting functional group such as the epoxy group and a proton-donating functional group, the solvent is limited to a non-proton-donating organic solvent, coating procedure is complicated, and the production process is complicated because it is necessary to strictly control moisture of the coating solution or the working area. In addition, there is a problem that the safety and the durability are insufficient in the method of Patent Literature 2 because the method utilizes the heparin or the like to give the antithrombogenicity.

SUMMARY

According to an exemplary aspect, disclosed is an antithrombotic material, comprising a copolymer configured to have 75% by mole to 25% by mole of a repeating unit (A) derived from diacetone(meth)acrylamide represented by the following formula (1):

Formula (1)

wherein $R^1$ is a hydrogen atom or a methyl group, and 25% by mole to 75% by mole of a repeating unit (B) derived from a monomer having at least one sulfonate group selected from the group consisting of 2-(meth)acrylamide-2-methyl-propane sulfonic acid, vinyl sulfate, allyl sulfate, styrenesulfonic acid, sulfoethyl(meth)acrylate, and sulfopropyl(meth)acrylate in a molecule, or a salt of the monomer, wherein the total amount of the repeating unit (A) and the repeating unit (B) is 100% by mole of the copolymer.

According to an exemplary aspect, disclosed is a medical device comprising a base material and a coating layer that coats the surface of the base material, wherein the coating layer includes an exemplary antithrombotic material.

According to an exemplary aspect, disclosed is an antithrombotic material which is excellent in the anticoagulant activity and can form a stable coating layer on a base material through a simple and mild coating process.

According to an exemplary aspect, the above-described problems can be ameliorated or solved by copolymerizing a monomer having a sulfonate group in a molecule and diacetone (meth)acrylamide and by setting the composition to be in a certain range.

According to an exemplary aspect, the antithrombotic material includes a copolymer configured to have 75% by mole to 25% by mole of a repeating unit (A) derived from diacetone(meth)acrylamide represented by the following formula (1) (wherein $R^1$ is a hydrogen atom or a methyl group) and 25% by mole to 75% by mole of a repeating unit (B) derived from a monomer having at least one sulfonate group selected from a group consisting of 2-(meth)acrylamide-2-methyl-propane sulfonic acid, vinyl sulfate, allyl sulfate, styrenesulfonic acid, sulfoethyl(meth)acrylate, and sulfopropyl (meth)acrylate in a molecule, or a salt of the monomer (the total amount of the repeating unit (A) and the repeating unit (B) is 100% by mole of the copolymer).

[Chem. 1]

(1)

DETAILED DESCRIPTION

An exemplary antithrombotic material includes a copolymer configured to have 75% by mole to 25% by mole of a repeating unit (A) derived from diacetone(meth)acrylamide represented by the following formula (1) (wherein $R^1$ is a hydrogen atom or a methyl group) (hereinafter, simply referred to as "repeating unit (A)") and 25% by mole to 75% by mole of a repeating unit (B) derived from a monomer having at least one sulfonate group selected from a group consisting of 2-(meth)acrylamide-2-methyl-propane sulfonic acid, vinyl sulfate, allyl sulfate, styrenesulfonic acid, sulfoethyl(meth)acrylate, and sulfopropyl(meth)acrylate in a molecule, or a salt of the monomer (hereinafter, simply referred to as "repeating unit (B)") (the total amount of the repeating unit (A) and the repeating unit (B) is 100% by mole of the copolymer).

[Chem. 2]

(1)

According to an exemplary aspect, it is possible to provide an antithrombotic material which is excellent in anticoagulant activity, further has blood compatibility and an antibiofilm property, and can form a stable and homogenous coating layer, by a simple coating process with a single operation without requiring heating.

For example, according to an exemplary aspect, it is possible to form a stable coating layer (capable of forming an homogenous coating layer, of which a polymer itself has anticoagulant activity, without any elution even in contact with blood) by a simple coating process with respect to various plastics or metal surfaces that configure medical device, by setting the composition of the repeating unit (A) derived from diacetone(meth)acrylamide and the repeating unit (B) derived from a monomer having a sulfonate group in a molecule or a salt of the monomer.

Furthermore, for example, the antithrombotic material has excellent blood compatibility and an antibiofilm property. The biofilm is referred to as a mucous film in which mucus is secreted and generated by microorganisms and is in a state where a plurality of types of microorganisms coexist in the film and form a complex (community) to be adhered on a solid surface. In general, it is known that bacteria in the biofilm are highly resistant to antibiotics or immunity than bacteria in the atmosphere and colonization of bacteria (the formation of the biofilm) on the surface of the medical device (for example, implanted devices) can cause a serious problem for a patient. For example, the biofilm formed in the medical device such as catheters, implants, artificial organs, and endoscopes can cause an infectious disease.

In contrast to the above, it has been confirmed that the surface of the base material coated with the antithrombotic material according to an exemplary aspect can suppress the growth and the proliferation of the microorganism such as *Pseudomonas aeruginosa* and can significantly prevent or suppress the formation of the biofilm. That is, according to an exemplary aspect, there is provided a method of inhibiting formation of the biofilm on the surface of the base material by coating the surface of the base material using the copolymer configured to have 75% by mole to 25% by mole of the repeating unit (A) derived from diacetone(meth)acrylamide represented by the above described formula (1) and 25% by mole to 75% by mole of the repeating unit (B) derived from a monomer having at least one sulfonate group selected from a group consisting of 2-(meth)acrylamide-2-methyl-propane sulfonic acid, vinyl sulfate, allyl sulfate, styrenesulfonic acid, sulfoethyl(meth)acrylate, and sulfopropyl(meth)acrylate in a molecule, or a salt of the monomer (the total amount of the repeating unit (A) and the repeating unit (B) is 100% by mole of the copolymer).

In the above-described general formula (1), $R^1$ is a hydrogen atom or a methyl group. The diacetone(meth)acrylamide as a monomer forming the repeating unit (A) shows a room temperature-crosslinking property. That is, a carbonyl group in the above-described general formula (1) can form a covalent bond by being reacted with a cross-linking agent under a mild condition. For this reason, the antithrombotic material containing a polymer that has the repeating unit (A) can be fixed on the surface of the base material under a mild condition without requiring heating or the like and impairing the physical property of the base material itself.

$R^1$ can be a hydrogen atom from the viewpoint of the anticoagulant activity, the (antithrombotic) blood compatibility and the antibiofilm property of the obtained polymer. The repeating unit (A) can be derived from diacetone acrylamide (DAAM).

Examples of a monomer that constitutes the repeating unit (B) and has the sulfonate group in a molecule (hereinafter, referred to as "monomer (b)") include 2-(meth)acrylamide-2-methyl-propane sulfonic acid, vinyl sulfate, allyl sulfate, styrenesulfonic acid, sulfoethyl(meth)acrylate, and sulfopropyl(meth)acrylate. The sulfonate group ($-SO_3H$) or a sulfate group ($-SO_4H$) in the monomer (b) may be present by forming a salt with a cation such as a sodium ion, a potassium ion or the like. The monomer (b) may be used alone or in a combination of two or more thereof.

Since the monomer (b) is water soluble or water swellable, the monomer (b) is different from an anticoagulant active substance such as heparin, heparan sulfate, or the like derived from a living body, is soluble in various aqueous solvents or organic solvents, and is further excellent in sterilization resistance.

In the aqueous solvent such as body fluid, the antithrombotic material can effectively exhibit the anticoagulant activity, the (antithrombotic) blood compatibility and the antibiofilm property by being swollen on the surface of the base material and by forming an interface (outermost layer) with the aqueous solvent.

The copolymer having the repeating unit (B) derived from the monomer (b) described above can exhibit an excellent anticoagulant activity, (antithrombotic) blood compatibility and antibiofilm property.

The antithrombotic material is a material having anticoagulant activity. A material having the anticoagulant activity refers to a material, the activated partial thromboplastin time (hereinafter, referred to as APTT) of which when the material is added to saline in an amount of 1.25 mg/mL, is equal to or longer than 50 seconds, for example, equal to or longer than 55 seconds, for example, equal to or longer than 60 seconds.

In addition, the antibiofilm material refers to a material that, after allowing the material-coated base material to stand for 7 days in a bacterial suspension (concentration: about $1\times10^6$ bacteria/ml) containing bacteria (for example, *Pseudomonas aeruginosa*, drug-resistant bacteria, or the like) that can form the biofilm, equal to or less than 100 bacteria which are adhered to the surface and forms biofilm are found in 500 $\mu m^2$ of a surface area and, for example, no bacteria are found therein.

Examples of the above-mentioned monomer (b) can include 2-(meth)acrylamide-2-methyl-propane sulfonic acid, vinyl sulfate, and styrenesulfonic acid, or salts thereof, and in an exemplary embodiment can include 2-(meth)acrylamide-2-methyl-propane sulfonic acid and styrenesulfonic acid, or salts thereof from the viewpoint of the anticoagulant activity, (antithrombotic) blood compatibility, and the antibiofilm property. That is, the repeating unit (B) can include a repeating unit derived from 2-(meth)acrylamide-2-methyl-propane sulfonic acid represented by the following formula (2) (wherein $R^2$ is a hydrogen atom or a methyl group) or styrenesulfonic acid represented by the following formula (3), or a salt thereof.

[Chem. 3]

(2)

[Chem. 4]

(3)

For example, the repeating unit (B) includes a repeating unit derived from 2-(meth)acrylamide-2-methyl-propane sulfonic acid or a salt thereof. In the above-described formula (2), $R^2$ can be a hydrogen atom from the viewpoint of the anticoagulant activity (antithrombotic), the blood compatibility and the antibiofilm property of the obtained polymer.

Examples of the salts in the above-described monomer (b) include an inorganic cation salt and an organic cation salt. As the inorganic cation salt, an alkali metal salt and an alkaline earth metal salt are exemplary, and among them, a sodium salt, a potassium salt, and a lithium salt are exemplary. As the organic cation salt, an ammonium salt is exemplary.

In an exemplary copolymer, with respect to the total repeating unit constituting the copolymer (100% by mole), the repeating unit (A) is 75% by mole to 25% by mole and the repeating unit (B) is 25% by mole to 75% by mole, and in this case, the total amount of the repeating unit (A) and the repeating unit (B) is 100% by mole of the copolymer. That is, the molar composition ratio of the repeating unit (A) to the repeating unit (B) (hereinafter, simply referred to as "molar ratio") is 75:25 to 25:75.

In a case where the molar composition ratio of the repeating unit (A) to the repeating unit (B) (A:B) is less than 25:75 (in a case where the ratio of A is less than 25% by mole), since the repeating unit (A) derived from the diacetone(meth)acrylamide is small, cross-linking becomes insufficient when coating the surface of the base material, thereby making it impossible to form a stable coating layer. On the other hand, the polymer in which the molar composition ratio of the repeating unit (A) to the repeating unit (B) (A:B) exceeds 75:25 (in a case where the ratio of A is more than 75% by mole) is not preferable because it is impossible to exhibit the anticoagulant activity (equal to or longer than 50 seconds of APTT), antithrombogenicity, the (antithrombotic) blood compatibility and the antibiofilm property due to a small percentage of the repeating unit (B).

In an exemplary embodiment, the molar composition ratio of the repeating unit (A) to the repeating unit (B) (A:B) is 30:70 to 70:30. In the copolymer formed from such a repeating unit (A) and a repeating unit (B), it is possible to achieve both excellent anticoagulant activity and coating property with a simple coating process by setting the composition of the repeating unit (A) and the repeating unit (B) to be in the above specified range. For example, the molar composition ratio of the repeating unit (A) to the repeating unit (B) can be 30:70 to 50:50 in view of the anticoagulant activity.

A terminal end of the copolymer is not particularly limited, is appropriately defined based on the type of raw material used, and can be a hydrogen atom. The configuration of the copolymer is not also limited, and may be any of a random copolymer, an alternating copolymer, a periodic copolymer, and a block copolymer. The random copolymer where cross-linking points are dispersed can be desirable from the viewpoint of the improvement of the film strength (strength of the cross-linking structure) after the coating to the base material.

The weight-average molecular weight of the copolymer can be 10,000 to 10,000,000, for example, in view of the solubility. Moreover, the weight-average molecular weight of the copolymer can be 1,000,000 to 10,000,000, for example, in view of the easiness for preparing a coating solution. The "weight-average molecular weight" is a value which is measured by gel permeation chromatography (GPC) using polyethylene oxide or pullulan as a standard substance.

The method for producing the copolymer is not particularly limited. For example, a method of copolymerizing the diacetone(meth)acrylamide as a monomer corresponding to the above-described repeating unit (A) and one or two or more monomer(s) selected from the above-described monomer (b) corresponding to the above-described repeating unit (B) by stirring and heating the diacetone(meth)acrylamide and the monomer(s) in a polymerization solvent together with a polymerization initiator can be used.

As a method for polymerizing the monomer, it is possible to employ a polymerization method such as radical polymerization, anionic polymerization, or cationic polymerization, and, for example, the radical polymerization as it is easy to be used in production.

The polymerization initiator is not particularly limited and a polymerization initiator may be used. A redox-based polymerization initiator is exemplary in view of excellent polymerization stability, and specifically, the redox-based polymerization initiator is obtained by combining a reducing agent such as sodium sulfite, sodium hydrogen sulfite, ascorbic acid or the like with an oxidizing agent, for example, persulfate such as potassium persulfate (KPS), sodium persulfate, and ammonium persulfate, and a peroxide such as hydrogen peroxide, t-butyl peroxide, and methyl ethyl ketone peroxide. The mixing amount of the polymerization initiator can be 0.0001% by mole to 1% by mole with respect to the above-described monomer (the total amount of the diacetone (meth)acrylamide and the monomer (b) is 100% by mole).

The polymerization temperature during the copolymerization can be set to 30° C. to 100° C. in view of controlling the molecular weight. For example, 30 minutes to 24 hours can be employed for the polymerization.

As the polymerization solvents, aqueous solvents such as water, alcohol, and polyethylene glycols can be used, and water is exemplary. The polymerization solvents may be used alone and in a combination of two or more thereof. The concentration of the monomer in the polymerization solvent can be 10% by weight to 90% by weight, for example, 15% by weight to 80% by weight, and, for example, 20% by weight to 80% by weight. The monomer concentration with respect to the polymerization solvent indicates the concentration of the total weight of the diacetone (meth)acrylamide and the monomer (b).

Furthermore, during the copolymerization, a chain-transfer agent, a polymerization rate modifier, a surfactant, and other additives may be appropriately used.

It is exemplary that the copolymer after the copolymerization be refined by a general refining method such as re-precipitation, dialysis, ultrafiltration, and an extraction method.

The antithrombotic material can be suitably used as a coating layer (surface modifying layer) that coats the base material by being coated (fixed) on the surface of the base material that constitutes the medical device. That is, according to an exemplary embodiment, it is possible to provide a medical device having a base material and a coating layer that coats the surface of the base material and contains the above-described antithrombotic material.

The coating layer containing the above-described antithrombotic material can give the excellent anticoagulant activity to the medical device, and further can give the antibiofilm property and (antithrombotic) blood compatibility to the medical device.

For example, the "coating" includes not only a form where the entire surface of the base material is completely covered with the antithrombotic material, but also a form where only a portion of the surface of the base material is covered with the antithrombotic material, that is, for example, the antithrombotic material is adhered to only a portion of the surface of the base material.

The method for coating (fixing) the surface of the base material with the antithrombotic material is not particularly limited, and examples thereof include a method for fixing the antithrombotic material on the surface of the base material by coating the surface of the base material with a reaction product obtained by reacting the antithrombotic material with the cross-linking agent.

That is, the coating layer can be formed with the reaction product obtained by reacting the material having the blood compatibility with the cross-linking agent. The reaction product (cross-linking substance) can be insolubilized on the surface of the base material, thereby being rigidly fixed thereon.

The cross-linking agent that can be used is not particularly limited as long as the cross-linking agent can form a covalent bond by being reacted with the carbonyl group in the repeating unit (A) derived from the diacetone(meth)acrylamide of the antithrombotic material, and can be a hydrazide compound having at least two hydrazine residues in a molecule. The coating layer can be formed with the reaction production obtained by reacting the above-described antithrombotic material and the hydrazide compound having at least two hydrazine residues in a molecule. The hydrazine residue forms the covalent bond by being reacted with the carbonyl group under a mild condition, for example, at room temperature, thereby enabling the rigid fixation of the antithrombotic material on the surface of the base material without impairing an originally required physical property of the base material itself. In addition, it is possible to use a proton-donating solvent in such reaction without requiring strict control of moisture of the working area during the reaction.

Examples of the hydrazide compound include adipic acid dihydrazide, carbohydrazide, 1,3-bis(hydrazinocarboethyl)-5-isopropyl hydantoin.

Examples of the hydrazide compound further include a polymer or a copolymer which is subjected to a treatment causing poly(meth)acrylic acid ester to have the hydrazine residue after polymerizing the poly(meth)acrylic acid ester, or a polymer or a copolymer which is subjected to a treatment in advance causing the poly(meth)acrylic acid ester to have the hydrazine residue in the state of monomer.

Among them, adipic acid dihydrazide is exemplary in view of the solubility to water.

The cross-linking reaction between the hydrazide compound and the antithrombotic material can be conducted at room temperature as described above and it is generally unnecessary to add any catalyst, but can be accelerated by adding water-soluble metal salt such as zinc sulfate, manganese sulfate, cobalt sulfate or the like, or by heating and drying the hydrazide compound and the antithrombotic material. The heating temperature when heating and drying the hydrazide compound and the antithrombotic material can be 40° C. to 150° C., for example, 40° C. to 60° C. in view of not impairing the physical property of the base material.

The ratio of cross-linking agent can be 1 part by weight to 200 parts by weight with respect to 100 parts by weight of the above-described copolymer and, for example, 10 parts by weight to 100 parts by weight.

The coating method when coating the surface of the base material with the reaction production between the antithrombotic material and the cross-linking agent is not particularly limited. For example, a method of reacting the antithrombotic material with the cross-linking agent after applying solution (coating solution) containing the antithrombotic material and/or the cross-linking agent to the surface of the base material is exemplary. Accordingly, the antithrombotic material is rigidly fixed on the surface of the base material by the insolubilization of the reaction product (cross-linking substance) on the surface of the base material. In addition, it is possible to obtain good elution resistance, peel resistance or the like because the cross-linking agent acts as a binder between the surface of the base material and the antithrombotic mate.

For example, there are (1) a method of reacting the antithrombotic material and the cross-linking agent after applying a solution containing the antithrombotic material and cross-linking agent to the surface of the base material, (2) a method of reacting the antithrombotic material and the cross-linking agent by applying a solution containing the cross-linking agent to the surface of the base material after applying a solution containing the antithrombotic material to the surface of the base material, and (3) a method of reacting the antithrombotic material and the cross-linking agent by applying a solution containing the antithrombotic material to the surface of the base material after applying a solution containing the cross-linking agent to the surface of the base material.

The method of the above-described (1) is exemplary from the viewpoint that it is possible to form the coating layer by a simple coating process with a single operation.

The method of applying the solution containing the antithrombotic material or the cross-linking agent to the surface of the base material is not particularly limited, and examples thereof include dip coating, spraying, spin coating, dripping, doctor blading, brushing, roll coater, air knife coating, curtain coating, wire bar coating, and gravure coating.

The solvent for dissolving the antithrombotic material and/or the cross-linking agent is not particularly limited. Examples thereof include alcohol based solvents such as methanol, ethanol, isopropanol, and butanol, water, and non-proton-donating organic solvents such as chloroform, tetrahydrofuran, acetone, dioxane, and benzene. The solvent may be used alone or in a mixed form of two or more thereof.

In an exemplary case where the solution containing the antithrombotic material and the solution containing the cross-linking agent are separately prepared (for example, in a case of the above-described (2) or (3)), a solvent can be selected that swells the base material as a solvent for dissolving the antithrombotic material in order to rigidly fix the antithrombotic material on the surface of the base material. The inside of the base material is impregnated with the antithrombotic material and the antithrombotic material is rigidly fixed thereto. On the other hand, a solvent that does not swell the base material too much can be used as a solvent for dissolving the cross-linking agent.

In addition, a solubilizing agent such as a surfactant, a lipid-solubilizing agent for solubilization in the organic solvent, or the like may be added to the coating solution as a third component.

For example, it is possible to coat the reaction product obtained by reacting the antithrombotic material and the cross-linking agent on the surface of the base material by applying the solution (coating solution) containing the antithrombotic material and/or the cross-linking agent to the surface of the base material and subsequently drying the applied solution at room temperature. The base material after the application may be dried by adding heat in order to improve adhesiveness between the base material and the antithrombotic material.

Another method may include fixing the antithrombotic material on the surface of the base material by removing the solvent after applying the solution (solution containing the antithrombotic material) obtained by dissolving the antithrombotic material in the solvent, to the surface of the base material.

The type or the form of the base material that can fix the antithrombotic material is not particularly limited. Examples of the type of the base material include various polymeric materials such as polyolefin, modified polyolefin, polyether, polyurethane, polyamide, polyimide, polyester, polytetrafluoroethylene, or polyvinyl chloride, and copolymer thereof, and metal, ceramic, carbon, and a composite material thereof. In addition, the form of the base material is not limited to a molding using one of the above-described materials alone, but blend moldings, alloying moldings, multilayered moldings, or the like can be used. When the antithrombotic material is to be rigidly fixed by swelling the base material using the solvent, above-described polymeric materials are exemplary as materials that exist at least on the surface of the base material because the polymeric materials can swell the base material using the solvent. In addition, it is exemplary that a proton-donating group be introduced to the entire base material or the surface of the base material in order to effectively fix the antithrombotic material via the cross-linking agent on the surface of the base material.

As the form of the base material, various forms such as a sheet-like form and a tube-like form can be used.

The medical device where the antithrombotic material is fixed comes into contact with blood, body fluids or a biological tissue. Examples of the medical device include an implantable prosthesis, therapeutic device (implant), extracorporeal cyclic type artificial organs, catheters, or guide wires. For example, there are implantable medical devices such as an artificial blood vessel, an artificial trachea, a stent, artificial skin, and artificial pericardium that can be inserted or replaced into the blood vessel or lumen; artificial organ systems such as an artificial heart system, an artificial lung system, an artificial kidney system, an artificial liver system, and an immune-regulation system; an indwelling needle; catheters which are inserted or indwelled into the blood vessel such as an IVH catheter, a liquid medicine administering catheter, a thermo-dilution catheter, an angiographic catheter, vasodilative catheter or a dilator, and an introducer, and a guide wire or a stylet for the catheters; and catheters inserted or indwelled into the biological tissue other than the blood vessel, such as a gastric catheter, a feeding catheter, and an elementary diet (ED) tube, a urethral catheter, a ureteral catheter, a balloon catheter, various suction catheters including an endotracheal suction catheter, and drainage catheters. For example, the medical device is suitably used as the artificial lung system coming into contact with a large amount of blood.

EXAMPLES

Hereinafter, aspects of the present disclosure will be described based on Examples, but the present disclosure is not limited thereto. Weight-average molecular weight of the polymer was measured using GPC (instrument: SHOWA DENKO K.K., GPC system; standard substance: pullulan).

Example 1

Synthesis of AMPS:DAAM=2:1

14.9 g (72 mmol) of 2-acrylamide-2-methyl-propane sulfonic acid (AMPS) and 6.1 g (36 mmol) of diacetone acrylamide (DAAM) were dissolved in 100 mL of pure water and the dissolved mixture was put in a four-necked flask to be subjected to nitrogen bubbling in an oil bath for an hour at the temperature of 50° C. Thereafter, 0.146 g (0.5% by mole with respect to the total molar amount of the AMPS and the DAAM) of potassium persulfate (KPS) and 0.068 g (the equimolar amount of the KPS) of sodium sulfite were dissolved in 2 mL of water and the solution where nitrogen purge was conducted was added thereto, to perform polymerization by stirring the mixture for 5 hours at the temperature of 50° C.

After the polymerization, the obtained aqueous solution was refined by putting the aqueous solution into a dialysis membrane (molecular weight cut off: 12,000 to 14,000) and by dialyzing it in reverse osmosis water for equal to or longer than 3 days. After the dialysis, a solid polymer (random copolymer) configured to have an AMPS-derived repeating unit and a DAAM-derived repeating unit was obtained by freeze-drying.

The weight-average molecular weight of the obtained solid polymer was 7,500,000. In addition, the composition of the AMPS and the DAAM of the solid polymer was measured by neutralization titration and the molar ratio of AMPS:DAAM was 2:1.

Example 2

Synthesis of AMPS:DAAM=1:1

11.1 g (54 mmol) of 2-acrylamide-2-methyl-propane sulfonic acid (AMPS) and 9.12 g (54 mmol) of DAAM were dissolved in 100 mL of pure water and the dissolved mixture was put in a four-necked flask to be subjected to nitrogen bubbling in an oil bath for an hour at the temperature of 50° C. Thereafter, 0.146 g (0.5% by mole with respect to the total molar amount of the AMPS and the DAAM) of potassium persulfate (KPS) and 0.068 g (the equimolar amount of the KPS) of sodium sulfite were dissolved in 2 mL of water and the solution where nitrogen purge was conducted was added thereto, to perform polymerization by stirring the mixture for 5 hours at the temperature of 50° C.

After the polymerization, the obtained aqueous solution was refined by putting the aqueous solution into a dialysis membrane (molecular weight cut off: 12,000 to 14,000) and by dialyzing it in reverse osmosis water for equal to or longer than 3 days. After the dialysis, a solid polymer (random copolymer) configured to have an AMPS-derived repeating unit and a DAAM-derived repeating unit was obtained by freeze-drying.

The weight-average molecular weight of the obtained solid polymer was 3,500,000.

In addition, the composition of the AMPS and the DAAM of the solid polymer was measured by neutralization titration and the molar ratio of AMPS:DAAM was 1:1.

Example 3

Synthesis of AMPS:DAAM=1:2

7.47 g (36 mmol) of 2-acrylamide-2-methyl-propane sulfonic acid (AMPS) and 12.2 g (72 mmol) of DAAM were dissolved in 100 mL of pure water and the dissolved mixture was put in a four-necked flask to be subjected to nitrogen bubbling in an oil bath for an hour at the temperature of 50° C. Thereafter, 0.146 g (0.5% by mole with respect to the total molar amount of the AMPS and the DAAM) of potassium persulfate (KPS) and 0.068 g (the equimolar amount of the KPS) of sodium sulfite were dissolved in 2 mL of water and the solution where nitrogen purge was conducted was added thereto, to perform polymerization by stirring the mixture for 5 hours at the temperature of 50° C.

The polymerization liquid was added dropwise to acetone and a white solid was generated. After performing decantation, the solid was dissolved in methanol. Then, the dissolved solution was precipitated in the acetone again. A solid polymer (random copolymer) configured to have the AMPS-derived repeating unit and the DAAM-derived repeating unit was obtained by performing suction-filtration and vacuum drying after performing the decantation again.

The weight-average molecular weight of the obtained solid polymer was 2,100,000. In addition, the composition of the AMPS and the DAAM of the solid polymer was measured by neutralization titration and the molar ratio of AMPS:DAAM was 1:2.

Comparative Example 1

Synthesis of AMPS:DAAM=1:8

2.49 g (12 mmol) of 2-acrylamide-2-methyl-propane sulfonic acid (AMPS) and 16.25 g (96 mmol) of DAAM were dissolved in 100 mL of pure water and the dissolved mixture was put in a four-necked flask to be subjected to nitrogen bubbling in an oil bath for an hour at the temperature of 50° C. Thereafter, 0.146 g (0.5% by mole with respect to the total molar amount of the AMPS and the DAAM) of potassium persulfate (KPS) and 0.068 g (the equimolar amount of the KPS) of sodium sulfite were dissolved in 2 mL of water and the solution where nitrogen purge was conducted was added thereto, to perform polymerization by stirring the mixture for 5 hours at the temperature of 50° C.

After dissolving the obtained white solid moiety in acetone and then stirring the dissolved solution overnight, the resultant was added dropwise to hexane. A solid polymer (random copolymer) configured to have the AMPS-derived repeating unit and the DAAM-derived repeating unit was collected by performing vacuum drying and removing the hexane after performing decantation.

The weight-average molecular weight of the obtained solid polymer was 1,200,000. In addition, the composition of the AMPS and the DAAM of the solid polymer was measured by neutralization titration and the molar ratio of AMPS:DAAM was 1:8.

Comparative Example 2

Synthesis of AMPS:DAAM=8:1

19.9 g (96 mmol) of 2-acrylamide-2-methyl-propane sulfonic acid (AMPS) and 2.03 g (12 mmol) of DAAM were dissolved in 100 mL of pure water and the dissolved mixture was put in a four-necked flask to be subjected to nitrogen bubbling in an oil bath for an hour at the temperature of 50° C. Thereafter, 0.146 g (0.5% by mole with respect to the total molar amount of the AMPS and the DAAM) of potassium persulfate (KPS) and 0.068 g (the equimolar amount of the KPS) of sodium sulfite were dissolved in 2 mL of water and the solution where nitrogen purge was conducted was added thereto, to perform polymerization by stirring the mixture for 5 hours at the temperature of 50° C.

After the polymerization, the obtained aqueous solution was refined by putting the aqueous solution into a dialysis membrane (molecular weight cut off: 12,000 to 14,000) and by dialyzing it in reverse osmosis water for equal to or longer than 3 days. After the dialysis, a solid polymer (random copolymer) configured to have an AMPS-derived repeating unit and a DAAM-derived repeating unit was obtained by freeze-drying.

The weight-average molecular weight of the obtained solid polymer was 8,900,000. In addition, the composition of the AMPS and the DAAM of the solid polymer was measured by neutralization titration and the molar ratio of AMPS:DAAM was 8:1.

Comparative Example 3

Synthesis of PMEA 26.3 g (0.2 mol) of 2-methoxyethyl acrylate (MEA) was dissolved in 100 mL of toluene and the dissolved mixture was put in a four-necked flask to be subjected to nitrogen bubbling in an oil bath for an hour at the temperature of 80° C. Thereafter, 0.03 g of azobisisobutyronitrile was dissolved in 2 mL of toluene and the solution where nitrogen purge was conducted was added thereto, to perform polymerization by stirring the mixture for 8 hours at the temperature of 80° C.

The polymerization liquid was added dropwise to hexane and a white viscous substance was generated. After performing decantation, the viscous substance was dissolved in acetone. After adding dropwise the dissolved substance to hexane again and performing decantation, the substance was dissolved in the acetone. The acetone was removed by vacuum drying the dissolved substance to collect a sticky polymer (PMEA).

The weight-average molecular weight of the obtained solid polymer was 100,000.

Example 4

Synthesis of Sodium Styrenesulfonate:DAAM=2:1

7.1 g (118 mmol) of sodium styrenesulfonate and 2.9 g (59 mmol) of DAAM were dissolved in 47 mL of pure water and the dissolved mixture was put in a four-necked flask to be subjected to nitrogen bubbling in an oil bath for an hour at the temperature of 50° C. Thereafter, 0.069 g (0.05% by mole with respect to the total molar amount of the sodium styrenesulfonate and the DAAM) of potassium persulfate (KPS) and 0.032 g (the equimolar amount of the KPS) of sodium sulfite were dissolved in 3 mL of water and the solution where nitrogen purge was conducted was added thereto, to perform polymerization by stirring the mixture for 5 hours at the temperature of 50° C. while continuously performing the nitrogen bubbling.

A white solid polymer (random copolymer) configured to have the sodium styrenesulfonate-derived repeating unit and the DAAM-derived repeating unit was collected by precipitating the polymerization liquid in acetone again and performing extraction via suction filtration after the polymerization. The obtained solid polymer was subjected to vacuum drying for 4 hours.

In addition, the composition of the sodium styrenesulfonate and the DAAM of the solid polymer was measured by neutralization titration and the molar ratio of sodium styrenesulfonate:DAAM was 2:1.

[Evaluation]

(Test 1-1. Measurement of Anticoagulation Time (Activated Partial Thromboplastin Time (APTT)))

APTT was measured through the following method using the polymers obtained from Examples 1 to 3 and Comparative Examples 1 and 3.

50 µL of a management blood plasma, 5 µL (1.25 mg/mL) of saline solution of a polymer to be measured, and 50 µL of an APTT reagent were dispensed into a cuvette, to which a steel ball was placed, warmed up to the temperature of 37° C., and then the mixture was allowed to stand for 180 seconds at the temperature of 37° C. Thereafter, 50 µL of a calcium chloride reagent was dispensed thereto to measure the time at which the vibration (amplitude) of the steel ball terminates. The measurement was performed twice and an average value thereof was employed (n=2).

The measurement was performed using a control which is configured to only have 50 µL of the management blood plasma and 50 µL of the APTT reagent. The result is shown in the following Table 1.

TABLE 1

| | Composition of Polymer to be Measured (Molar Ratio) Constituting Unit (B):Constituting Unit (A) | APTT (seconds) |
|---|---|---|
| Example 1 | AMPS:DAAM = 2:1 | 113 |
| Example 2 | AMPS:DAAM = 1:1 | 80 |

TABLE 1-continued

| | Composition of Polymer to be Measured (Molar Ratio) Constituting Unit (B):Constituting Unit (A) | APTT (seconds) |
|---|---|---|
| Example 3 | AMPS:DAAM = 1:2 | 58 |
| Comparative Example 1 | AMPS:DAAM = 1:8 | 41 |
| Comparative Example 3 | PMEA | 41 |
| Control (Management blood Plasma) | — | 41 |

From the above-described Table 1, it was confirmed that the polymers of Examples 1 to 3 of which the content of the AMPS corresponding to the repeating unit (B) (molar content with respect to the polymer (100% by mole)) is equal to or greater than 25% by mole, exhibit the anticoagulant activity as the coagulation time (APTT) is significantly extended compared to the control (management blood plasma).

On the other hand, the polymer of Comparative Example 1 of which the content of the AMPS (molar content with respect to the polymer (100% by mole)) is less than 25% by mole, did not show the effect of the extension of the coagulation time as its coagulation time (APTT) was the same as that of the control (management blood plasma).

In addition, it was confirmed from the comparison of Examples 1 to 3 that there is a tendency that the larger the content of the AMPS is, the greater the effect of the extension of the coagulation time (anticoagulant activity) is.

(Test 1-2. Measurement of Anticoagulation Time (Activated Partial Thromboplastin Time (APTT)))

APTT was measured through the following method using the polymer obtained from Example 4.

50 μL of a management blood plasma, 5 μL (1.25 mg/mL) of saline solution of a polymer to be measured, and 50 μL of an APTT reagent were dispensed into a cuvette, to which a steel ball was placed, warmed up to the temperature of 37° C., and then the mixture was allowed to stand for 180 seconds at the temperature of 37° C. Thereafter, 50 μL of a calcium chloride reagent was dispensed thereto to measure the time at which the vibration (amplitude) of the steel ball terminates. The measurement was performed twice and an average value thereof was employed (n=2).

The measurement was performed using a control which is configured to only have 50 μL of the management blood plasma and 50 μL of the APTT reagent. The result is shown in the following Table 2.

TABLE 2

| | Composition of Polymer to be Measured (Molar Ratio) Constituting Unit (B):Constituting Unit (A) | APTT (seconds) |
|---|---|---|
| Example 4 | sodium styrenesulfonate:DAAM = 2:1 | 130.4 |
| Control (Management blood Plasma) | — | 45.9 |

From the above-described Table 2, it was confirmed that the polymer of Example 4 of which the content of the sodium styrenesulfonate corresponding to the repeating unit (B) (molar content with respect to the polymer (100% by mole)) is equal to or greater than 25% by mole, exhibits the anticoagulant activity as the coagulation time (APTT) is significantly extended compared to the control (management blood plasma).

(Test 2-1. Coating Property Test 1: PP (Polypropylene) Sheet)
(1) Preparation of Coating Solution Coating solution was prepared by dissolving the polymers obtained from Examples 1 to 3 and Comparative Example 2 in a mixed solution of water:methanol (1:1 of a volume ratio) with a concentration of 1% by weight, and by adding adipic acid dihydrazide as a cross-linking agent at the same amount as the polymer (the same weight as the polymer itself).

(2) Formation of Coating Layer

A coating layer of a polymer was formed on a sheet base material by dip-coating the sheet base material made of polypropylene with the coating solution and subsequently drying the dip-coated sheet base material at room temperature. It was confirmed whether or not there are any coating speckles after dyeing the coating layer with a toluidine blue color as a cationic water-soluble pigment. The result is shown in the following Table 3.

(Test 2-2. Coating Property Test 2: PP (Polypropylene) Sheet)
(1) Preparation of Coating Solution Coating solution was prepared by dissolving the polymer obtained from Example 4 in a mixed solution of water:ethanol:methanol=6:3:1 (volume ratio) with a concentration of 1% by weight, and by adding adipic acid dihydrazide as a cross-linking agent at the same amount as the polymer (the same weight as the polymer itself).

(2) Formation of Coating Layer

A coating layer of a polymer was formed on a sheet base material by dip-coating the sheet base material made of polypropylene with the coating solution and subsequently drying the dip-coated sheet base material for 3 hours at room temperature.

It was confirmed whether or not there are any coating speckles after dyeing the coating layer with a toluidine blue color as a cationic water-soluble pigment. The result is shown in the following Table 3.

TABLE 3

| | Composition of Polymer to be Measured (Molar Ratio) Constituting Unit (B):Constituting Unit (A) | Presence or Absence of Coating speckles |
|---|---|---|
| Example 1 | AMPS:DAAM = 2:1 | None |
| Example 2 | AMPS:DAAM = 1:1 | None |
| Example 3 | AMPS:DAAM = 1:2 | None |
| Example 4 | sodium styrenesulfonate:DAAM = 2:1 | None |
| Comparative Example 2 | AMPS:DAAM = 8:1 | Yes |

From the above-described Table 3, it was confirmed that in the polymers of Examples 1 to 4 of which the content of the DAAM corresponding to the repeating unit (A) (molar content with respect to the polymer (100% by mole)) is equal to or greater than 25% by mole, a homogenous coating layer without any coating speckles can be obtained by the simple dip-coating.

On the other hand, it was confirmed that in the polymer of Comparative Example 2 of which the content of the DAAM (molar content with respect to the polymer (100% by mole)) corresponding to the repeating unit (A) is less than 25% by mole, there is a coating speckles and the coating layer is unstable.

(Test 2-3. Coating Property Test 3: Polyvinyl Chloride Tube)
(1) Preparation of Coating Solution Coating solution was prepared by dissolving the polymer obtained from Example 4 in a mixed solution of methanol:water=5:1 (volume ratio) with a concentration of 1% by weight, and by adding adipic acid dihydrazide as a cross-linking agent at the same amount as the polymer (the same weight as the polymer itself).
(2) Formation of Coating Layer A coating layer of a polymer was formed on a sheet base material by dip-coating the sheet base material made of polyvinyl chloride tube with the coating solution and subsequently drying the dip-coated sheet base material for 3 hours at room temperature.

It was confirmed whether or not there are any coating speckles after dyeing the coating layer with a toluidine blue color as a cationic water-soluble pigment.

The coating layer after the dyeing was dyed without any coating speckles. From the result, it was confirmed that it is possible to perform the coating without any speckles even in a case of using the polyvinyl chloride tube as a base material.
(Test 3-1. Blood Compatibility Test 1: Polyvinyl Chloride Tube)

The polymers of Examples 1 to 3 and Comparative Example 3 are respectively coated on inner surfaces of flexible PVC tubes having an inside diameter of 6 mm and an outside diameter of 9 mm.

Each tube was filled with 8 mL of human blood prepared with a heparin concentration of 0.2 U/mL and both ends of the tubes were connected using a connector made of polycarbonate to make a loop shape. The tubes were disposed in a cylindrical rotating apparatus to be rotated for 120 minutes at a velocity of 40 rotations per minute at room temperature. Thereafter, the blood was collected to measure the prothrombin fragment concentration using an EIA method. The result is shown in the following Table 4.

TABLE 4

|  | Composition of Polymer to be Measured (Molar Ratio) Constituting Unit (B):Constituting Unit (A) | Blood Concentration [ng/ml] of Prothrombin F1 + 2 After 120 Minutes of Circulation |
|---|---|---|
| Example 1 | AMPS:DAAM = 2:1 | 568 |
| Example 2 | AMPS:DAAM = 1:1 | 590 |
| Example 3 | AMPS:DAAM = 1:2 | 774 |
| Comparative Example 3 | PMEA | 1200 |

From the above-described Table 4, the production amount of prothrombin F1+2 as a parameter indicating the degree of coagulation system activation was significantly low in a case (Examples 1 to 3) of using AMPS-DAAM copolymers having predetermined compositions compared to a case (Comparative Example 3) of using PMEA used as the antithrombotic material in the related art. Accordingly, it was confirmed that the AMPS-DAAM copolymer having a predetermined composition has excellent blood compatibility.
(Test 3-2. Blood Compatibility Test 2: Artificial Lung)

The polymers obtained from Example 3 and Comparative Example 3 were dissolved in a mixed solution of water:methanol (1:1 of a volume ratio) with a concentration of 1% by weight. An artificial lung (made by TERUMO CORPORATION) was filled with the mixture through a blood import side and the artificial lung was allowed to stand for 120 seconds and the mixture was subsequently removed from the artificial lung. Then, the artificial lung was air-blow dried.

The artificial lung was incorporated in an extracorporeal circulation circuit and was filled with 200 ml of heparin-added fresh blood and 200 ml of lactate Ringer solution to perform perfusion for 3 hours at a rate of 500 ml/min at a blood temperature of 37° C. Then, the prothrombin fragment concentration (concentration of prothrombin fragment 1+2) as an index of the coagulation system activation in blood was measured using an EIA method. The result is shown in the following Table 5.

TABLE 5

|  | Composition of Polymer to be Measured (Molar Ratio) Constituting Unit (B):Constituting Unit (A) | Blood Concentration [ng/ml] of Prothrombin F1 + 2 After 180 Minutes of Circulation |
|---|---|---|
| Example 3 | AMPS:DAAM = 1:2 | 68 |
| Comparative Example 3 | PMEA | 97 |

It was confirmed that the polymer of Example 3 has characteristics that the prothrombin fragment concentration in blood as an index of the coagulation system activation is significantly low and the blood coagulation system activation is actively suppressed compared to the artificial lung coated with the polymer of Comparative Example 3.
(Test 4. Antithrombogenicity Test: Polyurethane Tube; Catheter Shape)

The polymers obtained from Example 3 and Comparative Example 3 are dissolved in a mixed solution of water:methanol (1:1 of a volume ratio) with a concentration of 1% by weight. After dip-coating the outer surface of the polyurethane tube having an outer diameter of 2 mm with the mixture, the dip-coated outer surface of the tube was dried for equal to or longer than 12 hours at room temperature. Thereafter, the dried outer surface of the tube was allowed to stand in heparin-added fresh blood for two hours, was washed with saline, was fixed with glutaraldehyde, and then, the outer surface of the tube was observed using an electron microscope.

Figure 1A:
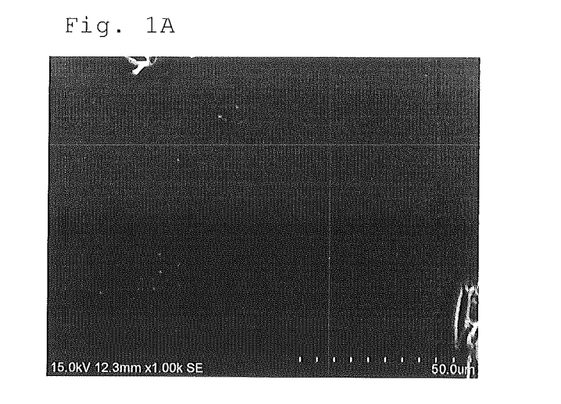
FIG. 1A is a drawing that shows an electro micrograph in an antithrombogenic test of a polymer obtained in Example 3, according to an exemplary aspect.
Figure 1B:
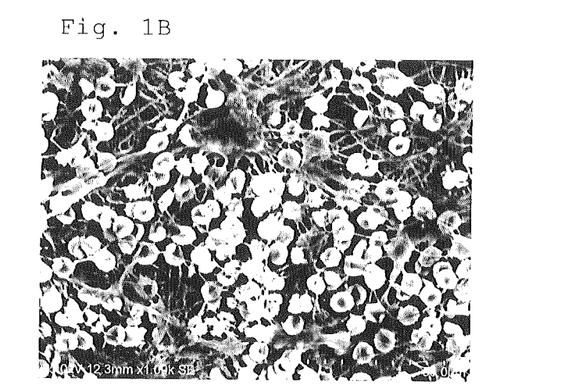
FIG. 1B is a drawing that shows an electro micrograph in an antithrombogenic test of a polymer obtained in Comparative Example 3, according to an exemplary aspect.

The result is shown in FIG. 1A and FIG. 1B.

There was no adhesion of a blood cell or the like in a case (FIG. 1A) of coating the outer surface with the polymer obtained from Example 3. In contrast to this, there were many blood cells adhered on the surface in a case (FIG. 1B) of coating the surface with the polymer obtained from Comparative Example 3. Accordingly, it was found that the AMPS-DAAM copolymer having a predetermined composition has excellent antithrombogenicity compared to the PMEA as an antithrombotic material of the related art (Comparative Example 3).
(Test 5. Antibiofilm Property Test)

The polymers obtained from Example 3 and Comparative Example 3 are dissolved in a mixed solution of water:methanol (1:1 of a volume ratio) with a concentration of 1% by weight. After dip-coating a surface of a 2 cm×5 cm polyurethane sheet with the mixture, the dip-coated surface of the polyurethane sheet was dried for equal to or longer than 12 hours at room temperature.

A coated test specimen was put in a bacterial suspension (about $1 \times 10^6$ bacteria/ml) to which *Pseudomonas aeruginosa* is suspended in a Soybean Casein Digest medium for sterility testing (made by SYSMEX bioMérieux Co., Ltd.) for 7 days and was allowed to stand in an incubator at the temperature of 32° C. The test specimen was washed with saline, was fixed with glutaraldehyde, and then, the surface was observed using an electron microscope.

Figure 2A:
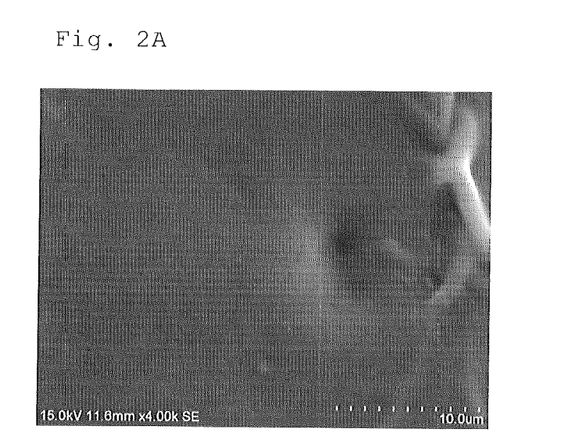
FIG. 2A is a drawing that shows an electro micrograph in an antibiofilm property test of a polymer obtained in Example 3, according to an exemplary aspect.
Figure 2B:
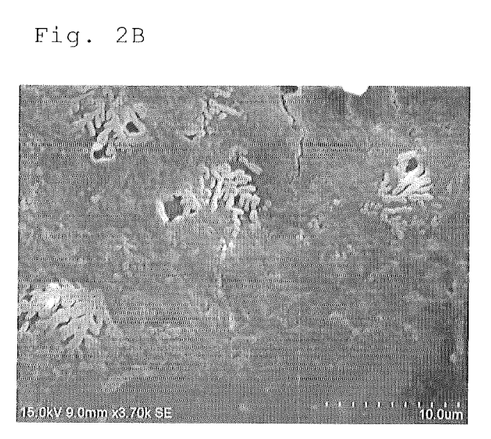
FIG. 2B is a drawing that shows an electro micrograph in an antibiofilm property test of a polymer obtained in Comparative Example 3, according to an exemplary aspect.

The result is shown in FIG. 2A and FIG. 2B.

There was neither adhesion of the *Pseudomonas aeruginosa* nor formation of the biofilm in 500 $\mu m^2$ of a surface area of the surface (FIG. 2A) coated with the polymer obtained from Example 3. In contrast to this, there was formation of the biofilm due to *Pseudomonas aeruginosa* in 500 μm² of a surface area of the surface (FIG. 2B) coated with the polymer obtained from Comparative Example 3. Accordingly, it was confirmed that the AMPS-DAAM copolymer having a predetermined composition has an excellent antibiofilm property compared to the PMEA as an antithrombotic material of the related art.

What is claimed is:

1. An antithrombotic material, comprising a copolymer consisting of 75% by mole to 25% by mole of a repeating unit (A) derived from diacetone (meth)acrylamide represented by the following formula (1):

Formula (1)

wherein $R^1$ is a hydrogen atom or a methyl group, and 25% by mole to 75% by mole of a repeating unit (B) derived from a monomer having at least one sulfonate group selected from the group consisting of 2-(meth)acrylamide-2-methyl-propane sulfonic acid, vinyl sulfate, allyl sulfate, styrenesulfonic acid, sulfoethyl (meth)acrylate, and sulfopropyl (meth)acrylate in a molecule, or a salt of the monomer,
wherein the total amount of the repeating unit (A) and the repeating unit (B) is 100% by mole of the copolymer.

2. The antithrombotic material according to claim 1, wherein the repeating unit (B) includes a repeating unit derived from 2-(meth)acrylamide-2-methyl-propane sulfonic acid or a salt thereof represented by the following formula (2):

Formula (2)

(2)

wherein $R^2$ is a hydrogen atom or a methyl group.

3. The antithrombotic material according to claim 2, wherein $R^1$ is a hydrogen atom in the formula (1), and $R^2$ is a hydrogen atom in the formula (2).

4. The antithrombotic material according to claim 1, wherein a molar ratio of the repeating unit (A) to the repeating unit (B) is 30:70 to 70:30.

5. The antithrombotic material according to claim 1, wherein a molar ratio of the repeating unit (A) to the repeating unit (B) is 30:70 to 50:50.

6. The antithrombotic material according to claim 1, wherein a weight-average molecular weight of the copolymer is 10,000 to 10,000,000.

7. A medical device comprising a base material and a coating layer that coats the surface of the base material, wherein the coating layer includes the antithrombotic material according to claim 1.

8. A medical device comprising a base material and a coating layer that coats the surface of the base material, wherein the coating layer includes the antithrombotic material according to claim 2.

9. A medical device comprising a base material and a coating layer that coats the surface of the base material, wherein the coating layer includes the antithrombotic material according to claim 3.

10. A medical device comprising a base material and a coating layer that coats the surface of the base material, wherein the coating layer is formed with a reaction product obtained by reacting the antithrombotic material according to claim 1 and a cross-linking agent.

11. A medical device comprising a base material and a coating layer that coats the surface of the base material, wherein the coating layer is formed with a reaction product obtained by reacting the antithrombotic material according to claim 2 and a cross-linking agent.

12. A medical device comprising a base material and a coating layer that coats the surface of the base material, wherein the coating layer is formed with a reaction product obtained by reacting the antithrombotic material according to claim 3 and a cross-linking agent.

13. The medical device according to claim 10, wherein the cross-linking agent is a hydrazide compound having at least two hydrazide residues per molecule.

14. The medical device according to claim 11, wherein the cross-linking agent is a hydrazide compound having at least two hydrazide residues per molecule.

15. The medical device according to claim 12, wherein the cross-linking agent is a hydrazide compound having at least two hydrazide residues per molecule.

16. The medical device according to claim 7, wherein the medical device is an implantable prosthesis, therapeutic device, an extracorporeal cyclic artificial organ, a catheter, or a guide wire.

17. The medical device according to claim 8, wherein the medical device is an implantable prosthesis, therapeutic device, an extracorporeal cyclic artificial organ, a catheter, or a guide wire.

18. The medical device according to claim 9, wherein the medical device is an implantable prosthesis, therapeutic device, an extracorporeal cyclic artificial organ, a catheter, or a guide wire.

* * * * *